US00PP21270P2

(12) United States Plant Patent
Meilland

(10) Patent No.: US PP21,270 P2
(45) Date of Patent: Sep. 7, 2010

(54) FLORIBUNDA ROSE PLANT NAMED 'MEILATHERY'

(50) Latin Name: *Rosa hybrida*
Varietal Denomination: Meilathery

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/585,429

(22) Filed: Sep. 15, 2009

(51) Int. Cl.
*A01H 5/00* (2006.01)

(52) U.S. Cl. ..... Plt./144
(58) Field of Classification Search ..... Plt./144
See application file for complete search history.

*Primary Examiner*—Annette H Para
(74) *Attorney, Agent, or Firm*—Buchanan Ingersoll & Rooney PC

(57) ABSTRACT

A new and distinct Floribunda rose plant is provided which forms attractive cream-white blossoms having five petals. The plant exhibits very strong vegetation, a semi-erect growth habit, and medium green foliage with a semi-glossy aspect. The disease tolerance is good particularly with respect to *Marsonina rosae*. The attractive green foliage contrasts nicely with the cream-white blossom coloration. The new variety is well suited for growing as attractive ornamentation in parks and gardens.

1 Drawing Sheet

Figures 1, 2, 3, 4, 5, 6, 7, 8, 9, 10, 11, 12, 13, 14, 15:
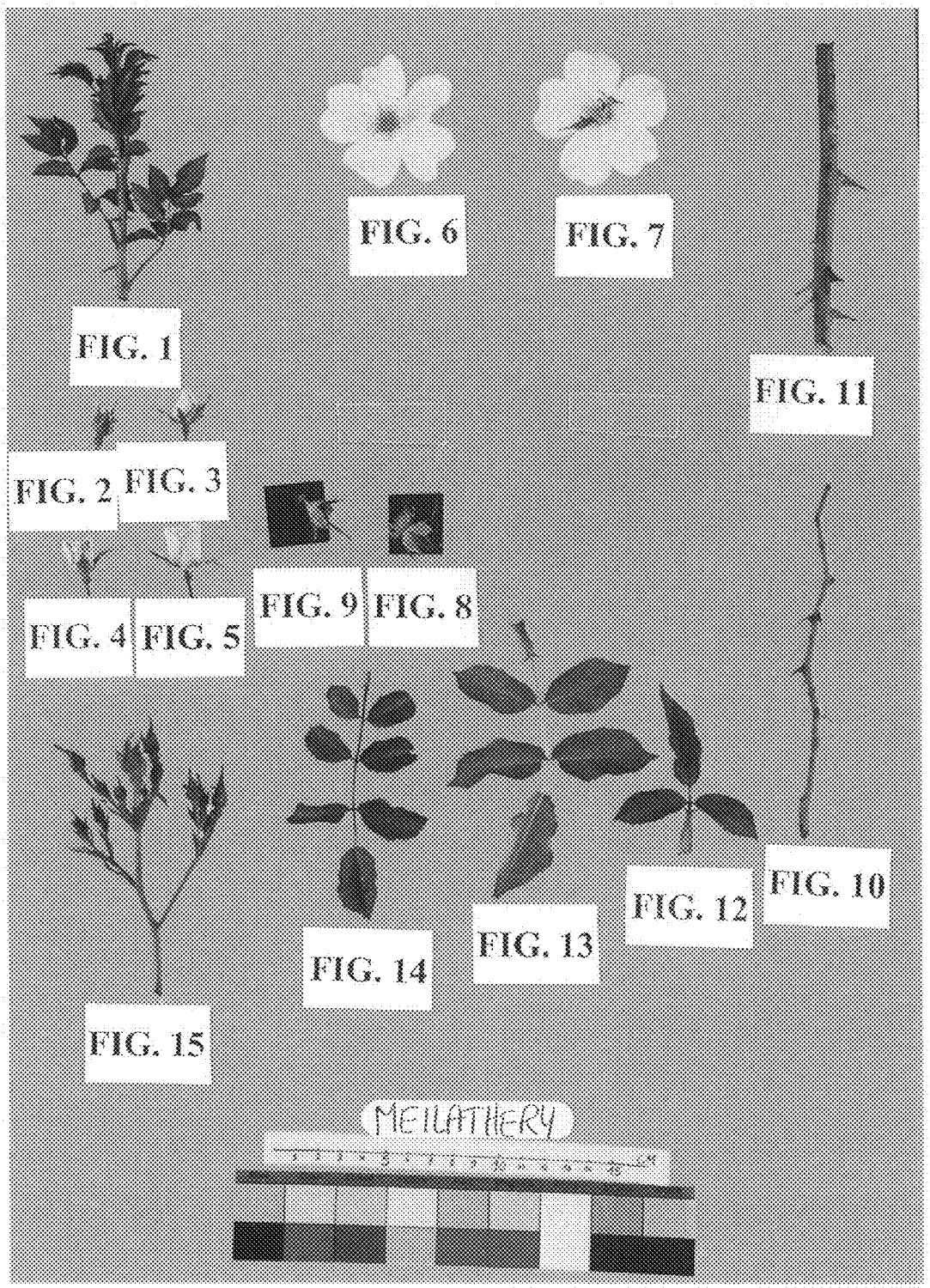

Botanical/commercial classification: *Rosa hybrida*/Floribunda Rose Plant.

Varietal denomination: cv. Meilathery.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'Korimro' variety (non-patented in the United States). The male parent (i.e., the pollen parent) was the product of the cross of the 'Meilontig' variety (U.S. Plant Pat. No. 6,598) and the 'Kormarie' variety (non-patented in the United States. The parentage of the new variety can be summarized as follows:

'Korimro'×('Meilontig'×'Kormarie').

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a semi-erect growth habit,
(b) forms in abundance on a recurrent basis attractive cream-white blossoms having five petals,
(c) forms attractive medium green semi-glossy foliage,
(d) displays good tolerance to disease, and
(e) is well suited for growing as ornamentation in parks and gardens.

The disease tolerance is particularly good with respect to *Marsonina rosae*. The medium green foliage coloration contrasts nicely with the cream-white blossom coloration.

The new variety well meets the needs of the horticultural industry and can be grown to advantage in the landscape where attractive ornamentation is desired.

The new variety can be readily distinguished from its ancestors. For instance, the 'Korimro' variety displays light pink to near white blossoms. The 'Meilontig' variety displays a more spreading growth habit with arching canes that tend to become more horizontal as the plant matures. The 'Kormarie' variety forms dissimilar yellow-tipped with red blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meilathery'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately four years of age and were observed during July while budded on *Rosa laxa* understock and growing outdoors at Le Cannet des Maures, Var, France. Dimensions in centimeters are indicated at the bottom of the photograph together with comparative color information.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of a fully open flower—plan view—obverse;

FIG. 7—illustrates a specimen of a fully open flower—plan view—reverse;

FIG. 8—illustrates a specimen of a floral receptacle showing the arrangement of the stamens and pistils;

FIG. 9—illustrates a specimen of a floral receptacle showing the arrangement of the pistils (stamens removed);

FIG. 10—illustrates a specimen of a flowering stem;

FIG. 11—illustrates a specimen of a main branch;

FIG. 12—illustrates a specimen of a leaf with three leaflets—plan view—upper surface;

FIG. 13—illustrates a specimen of a leaf with five leaflets—plan view—under surface;

FIG. 14—illustrates a specimen of a leaf with seven leaflets—plan view—upper surface; and FIG. 15—illustrates a specimen of a cluster of buds.

DETAILED DESCRIPTION

The chart used in the identification of the colors is that of The Royal Horticultural Society (R.H.S. Colour Chart), London, England. Common color terms are to be accorded their customary dictionary significance. The description is based on the observation of four-year-old plants during October while budded on *Rosa laxa* understock and growing outdoors at Le Gannet des Maures, Var, France.

Class: Floribunda.

Plant:

*Habit.*—Semi-erect.

Branches:

*Color.*—Young stems: near Yellow-Green Group 146B suffused with Greyed-Red Group 178A. Adult wood: near Yellow-Green Group 146B.

*Thorns.*—On young stems: Small prickles: commonly absent. Long prickles: configuration: very elongated and curved downwards on the upper surface, hooked on the under surface, and oval and long at the base. quantity: approximately 9 on average on a stem length of 10 cm. length: approximately 1.2 cm on average. color: near Greyed-Purple Group 183B. On adult stems: Small prickles: commonly absent. Long prickles: configuration: rather upright and rather elongated on the upper surface, slightly concave on the under surface, and large oval and long at the base. quantity: approximately 17 on average on a stem length of 18 cm. length: approximately 1.1 cm on average. color: near Greyed-Red Group 178A.

Leaves:

*Stipules.*—Adnate, pectinate, and rather broad, approximately 1.3 cm in length on average, approximately 6 mm in width on average, near Green Group 141B on the upper surface, and near Green Group 143A on the under surface.

*Petioles.*—Upper surface: slightly glandular, and near Green Group 137B in coloration. Under surface: bear some small prickles, and near Green Group 141B in coloration. Length: approximately 2.8 cm on average on the terminal leaflet.

*Rachis.*—Upper surface: near Green Group 137C in coloration. Under surface: near Green Group 143A in coloration. Texture: slightly glandular with small prickles.

*Leaflets.*—Number 3, and most often 5 and 7. Shape: generally oval with a rounded base and an acuminate tip. Size: the terminal leaflets commonly are approximately 4 cm in length on average, and approximately 2.3 cm in width on average. Serration: small and single (as illustrated). Texture: physically firm and thick. General appearance: rather dense with a semi-glossy aspect on the upper surface. Color (young foliage): upper surface: near Green Group 141A. under surface: near Yellow-Green Group 146D. Color (adult foliage): upper surface: near Green Group 137B. under surface: near Yellow-Green Group 146B.

Inflorescence:

*Number of flowers.*—Commonly approximately 6 to 12 flowers per stem.

*Peduncle.*—Smooth, near Yellow-Green Group 147B in coloration, approximately 2.9 cm in length on average, and approximately 0.2 cm in diameter on average.

*Sepals.*—Upper surface: tomentose and near Green Group 143B in coloration. Under surface: tomentose and near Green Group 141B in coloration. Shape: longish and narrow, and upright at the base. Configuration: approximately 2.4 cm in length on average, and approximately 0.7 cm in width on average at the widest point.

*Buds.*—Shape: elongated. Size: medium. Length: approximately 1.2 cm on average. Width: approximately 8 mm on average at the widest point. Color: upper surface: near Yellow Group 11A as the calyx breaks. under surface: near Yellow Group 10B as the calyx breaks.

*Flower.*—Shape: cup-shaped. Diameter approximately 5 to 7 cm on average when open. Color (in the course of opening): upper surface: Yellow-Orange Group 19B undersurface: near Yellow-Orange Group 18B suffused with near Orange Group 27A. basal petal spot: near Yellow Group 5B on the upper surface and near Yellow Group 9C on the under surface. Color (when fully open): upper surface: near White Group 155C. under surface: near White Group 155C. basal petal spot: near Yellow Group 5B on the upper surface and near Yellow Group 9C on the under surface. Fragrance: none. Petal shape: rounded base and a cuneiform tip. Petal number: 5 under normal growing conditions. Petal length: approximately 3.4 cm on average. Petal width: approximately 3.2 cm on average. Petal texture: leathery and firm. Petal arrangement: imbricated, and without petaloids. Petal drop: good with the petals commonly detaching cleanly before drying. Stamen number. approximately 156 on average. Anthers: regularly arranged around the styles, approximately 2 mm in size on average, and near Yellow-Orange Group 15B in coloration. Pollen: present. Filaments: approximately 0.6 cm in length on average, and near Yellow Group 7D in coloration. Pistils: approximately 30 on average. Stigmas: approximately 1 mm in size on average, and near Yellow Group 11B in coloration. Styles: approximately 5 mm in length on average, and near Yellow-Green Group 150D in coloration. Receptacle: smooth, pitcher-shaped in longitudinal section, approximately 6 mm in length on average, approximately 4 mm in width on average at the widest point, and near Green Group 143B in coloration.

Development:

*Vegetation.*—Very strong.

*Blooming.*—Somewhat late, abundant and recurrent.

*Tolerance to diseases.*—Very good, particularly with respect to *Marsonina rosae.*

I claim:

1. A new and distinct Floribunda rose plant characterized by the following combination of characteristics:

(a) exhibits a semi-erect growth habit, (b) forms in abundance on a recurrent basis attractive cream-white blossoms having five petals, (c) forms attractive medium green semi-glossy foliage, (d) displays good tolerance to disease, and (e) is well suited for growing as ornamentation in parks and gardens; substantially as herein shown and described.

* * * * *

MEILATHERY